(12) United States Patent
DeCesare et al.

(10) Patent No.: US 7,244,256 B2
(45) Date of Patent: Jul. 17, 2007

(54) ELECTROSURGICAL DEVICE WITH ADHESIVE-FREE INSULATING PIECE AND METHOD OF MAKING SAME

(75) Inventors: Michael DeCesare, New Port Richey, FL (US); Hugh S. West, Jr., Sandy, UT (US)

(73) Assignee: Linvatec Corporation, Largo, FL (US)

( * ) Notice: Subject to any disclaimer, the term of this patent is extended or adjusted under 35 U.S.C. 154(b) by 505 days.

(21) Appl. No.: 10/866,371

(22) Filed: Jun. 10, 2004

(65) Prior Publication Data

US 2005/0277916 A1 Dec. 15, 2005

(51) Int. Cl.
A61B 18/14 (2006.01)

(52) U.S. Cl. ......................... 606/41; 606/49
(58) Field of Classification Search ................. 606/41, 606/49
See application file for complete search history.

(56) References Cited

U.S. PATENT DOCUMENTS

| | | | |
|---|---|---|---|
| 3,828,780 A | 8/1974 | Morrison, Jr. | |
| 4,674,498 A * | 6/1987 | Stasz ........................... | 606/48 |
| 4,998,933 A | 3/1991 | Eggers et al. | |
| 5,178,620 A | 1/1993 | Eggers et al. | |
| 5,308,311 A * | 5/1994 | Eggers et al. ................. | 600/28 |
| 5,364,395 A | 11/1994 | West, Jr. | |
| 5,366,443 A | 11/1994 | Eggers et al. | |
| 5,419,767 A | 5/1995 | Eggers et al. | |
| 5,472,441 A | 12/1995 | Edwards et al. | |
| 5,542,945 A * | 8/1996 | Fritzsch ....................... | 606/48 |
| 5,681,282 A * | 10/1997 | Eggers et al. ................. | 604/114 |
| 5,697,909 A | 12/1997 | Eggers et al. | |
| 5,904,681 A | 5/1999 | West, Jr. | |
| 6,168,593 B1 * | 1/2001 | Sharkey et al. ............... | 606/34 |
| 6,190,381 B1 | 2/2001 | Olsen et al. | |
| 6,238,391 B1 * | 5/2001 | Olsen et al. .................. | 606/41 |
| 6,254,600 B1 * | 7/2001 | Willink et al. ................ | 606/41 |
| 6,296,638 B1 | 10/2001 | Davison et al. | |
| 6,379,350 B1 * | 4/2002 | Sharkey et al. ............... | 606/41 |
| 6,461,357 B1 * | 10/2002 | Sharkey et al. ............... | 606/45 |
| 6,482,201 B1 | 11/2002 | Olsen et al. | |
| 6,565,561 B1 * | 5/2003 | Goble et al. .................. | 606/41 |
| 6,589,237 B2 | 7/2003 | Woloszko et al. | |
| 6,618,626 B2 | 9/2003 | West, Jr. et al. | |
| 6,645,203 B2 * | 11/2003 | Sharkey et al. ............... | 606/41 |
| 2002/0120267 A1 * | 8/2002 | Phan ........................... | 606/51 |
| 2003/0153906 A1 * | 8/2003 | Sharkey et al. ............... | 606/41 |

OTHER PUBLICATIONS

Arthrocare: Multi-Electrode Technology (published on or before May 2004).

* cited by examiner

Primary Examiner—Michael Peffley
Assistant Examiner—Alex B. Toy
(74) Attorney, Agent, or Firm—Workman Nydegger

(57) ABSTRACT

An electrosurgical device having an electrode and an insulating piece such as a ceramic insulator is disclosed. The electrode includes an active surface for ablating and/or coagulating tissue in an electrosurgical procedure. The insulating piece surrounds the active surface and provides a barrier for the intense heat created during ablation. The insulating piece is also electrically nonconductive to prevent unwanted discharge of energy. Electrode has a retaining ledge configured to engage a lip formed on the insulating ring. The insulating ring is secured to the electrosurgical device by connecting the electrode to an electrode seat and capturing the insulating piece in between. The electrode can be connected to the electrode seat by projection welding. The insulating piece is connected to the electrode without the use of an adhesive.

22 Claims, 5 Drawing Sheets

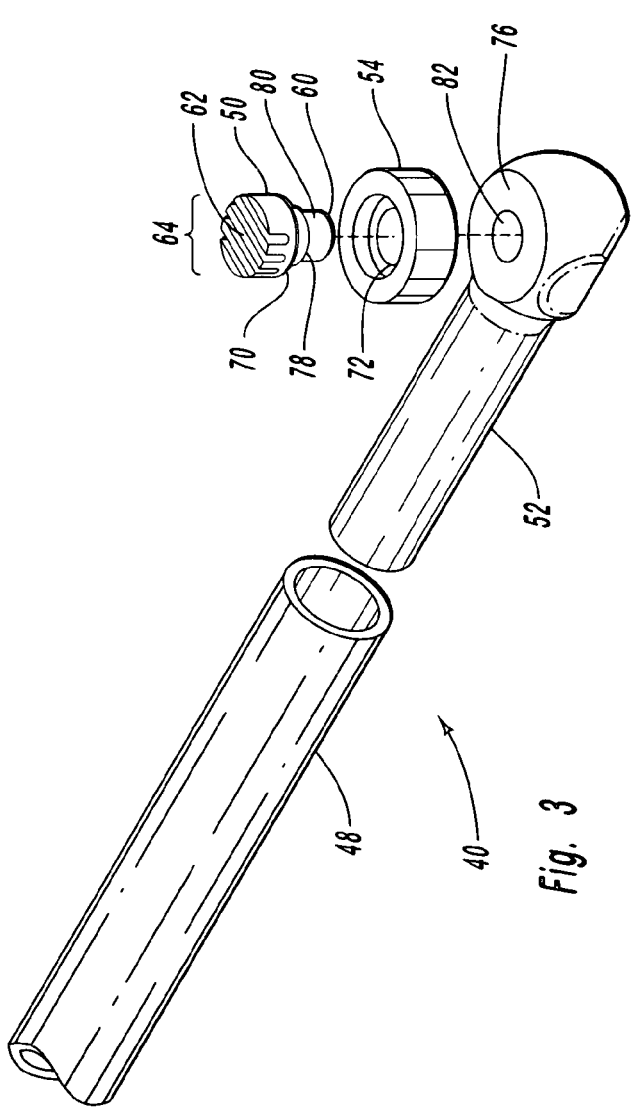
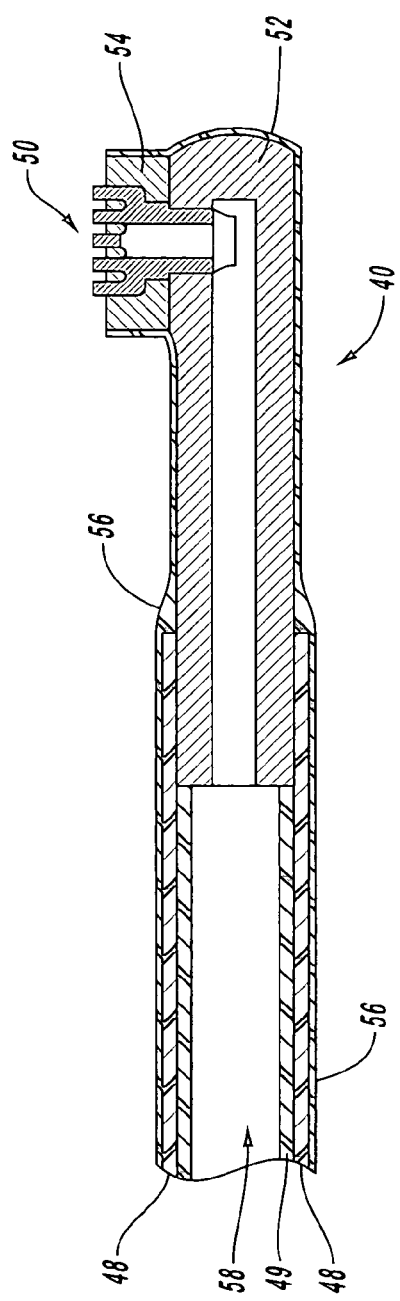
Fig. 3
Fig. 4

ELECTROSURGICAL DEVICE WITH ADHESIVE-FREE INSULATING PIECE AND METHOD OF MAKING SAME

BACKGROUND OF THE INVENTION

1. The Field of the Invention

The present invention relates to electrosurgical devices for ablating tissue in a surgical procedure. More specifically, the present invention relates to electrosurgical devices with an adhesive-free insulating piece surrounding the electrode.

2. The Relevant Technology

An arthroscope is an instrument used to look directly into a surgical site. Typically, the arthroscope utilizes a magnifying lens and coated glass fibers that beam an intense, cool light into the surgical site. A camera attached to the arthroscope allows the surgeon to view the surgical site on a monitor in the operating room. With the arthroscope, the surgeon can look directly into a surgical site, such as a knee or shoulder, to diagnose injury and decide on the best treatment. While viewing the surgical site with the arthroscope, the surgeon can repair an injury using a separate surgical instrument.

The ability to view the surgical site in this manner allows for a minimally invasive procedure. In recent years, arthroscopic surgeries have been developed for surgical procedures that traditionally were once very complicated and time consuming. Many of these surgeries are now performed as outpatient procedures using arthroscopic techniques.

At the beginning of the arthroscopic procedure, the patient receives an anesthetic. After the patient has been sufficiently anesthetized, the surgeon makes a plurality of incisions, known as portals, from the exterior of the body of the patient to the surgical site. Three portals are usually made: a first for the arthroscope, a second for the surgical instrument, and a third to permit fluids to escape from the surgical site. Sterile fluid is generally introduced by way of the arthroscope through the first portal. The sterile fluid serves among other purposes to expand the area of the surgical site. The insertion of sterile fluid makes it easier to see and work inside the body of the patient at the surgical site.

Electrosurgical instruments are a common device used in arthroscopy to ablate and/or coagulate tissue. In electrosurgery, an electrode is used to direct a high frequency current near or through body tissue. The high frequency current generates enough heat to ablate tissue. In monopolar electrosurgery the return electrode is a patch placed on the person. Energy that dissipates into the tissue connects the circuit by passing through the patch.

In a bipolar electrosurgical device, the return electrode is placed in a separate location on the electrosurgical device. Energy leaving the ablator electrode passes through fluids and/or tissue and returns to the return electrode on the electrosurgical device.

In both monopolar and bipolar electrosurgery, an electrode transfers energy to the surrounding fluid. The energy can be controlled to simply warm the adjacent tissue or to cut or ablate the tissue. Warming tissue is often done to facilitate coagulation. The heating event causes coagulation and thus can be used to stop bleeding in an arthroscopic procedure.

To ablate tissue, larger amounts of energy are applied to the electrode. The electrode generates enough heat to create gas bubbles around the electrode. The gas bubbles have a much higher resistance than tissue or saline, which causes the electrode voltage to increase. Given sufficient power the electrode discharges (i.e. arcs). The high voltage current travels through the gas bubbles and creates a plasma discharge over the surface of the electrode. Moving the electrode close to tissue causes the plasma discharge to come within a distance sufficiently close to ablate the tissue.

The contours and surface area of an electrode are important for controlling where arcing occurs on the electrode and how much power is required to cause a discharge. Current density is greatest at sharp edges. Arcing, and thus ablating, can be controlled by forming electrodes or electrode edges with small surface areas.

Typically, edges or small surface areas are created on an electrode by forming grooves or placing small wires. An important aspect of an electrode is that non-active surfaces must be electrically isolated from material such as the electrically conductive saline on the exterior of the electrode. Electrical conduction to these materials can ground the circuit and prevent the electrode from delivering its current to the active surface. For example wires or conducting materials that deliver current through the probe to the active surface need to be electronically isolated from the exterior of the probe, which can come into contact with body tissues during a procedure.

Much of the length of an electrosurgical probe is coated with an insulator or has lead wires that run inside insulated tubing. Near the active surface, however, insulating the electrodes becomes more difficult because of the extreme heat generated by the active surface. Many existing electrosurgical devices use an insulator such as a ceramic piece to protect the active portion of the electrode. For example electrodes that use multiple pins typically have a ceramic piece with holes for each of the pins. The pins are inserted through the holes and then the ceramic piece is glued to the probe's tubing using a temperature resistant adhesive.

Likewise, many single piece electrodes use a ceramic ring that encircles the active portion of the electrode. Typically the electrode is welded to an electrode seat or other tubing. The ceramic piece is then placed around the active portion of the electrode and glued using a temperature resistant adhesive.

Often, the ceramic piece only covers a small portion of the electrode near the active portion of the electrode. This practice is due to the fact that the extreme temperatures reached by the active surface dissipate very rapidly with distance away from the active surface. After a small distance other materials which are less resistant to temperature can be used as an insulator.

One problem with gluing the insulating piece to the probe using a temperature resistant adhesive is that the adhesive bonds can fail due to local high temperatures. Although the failure rates of the insulating piece are somewhat low, the consequences of the ceramic piece failing are very undesirable. If an insulating piece breaks off it falls into the operating cavity. Surgeons are often reluctant to leave foreign material in a person's body and thus spend precious time looking for the piece through the arthroscope. Furthermore, failure of the insulating piece is undesirable because it requires the surgeon to replace the instrument, thus increasing costs.

Another disadvantage of gluing the ceramic piece to the electrode is the expense incurred to manufacture the electrode. Electrosurgical probes are very small and asseyymbled by hand. Gluing a small insulating piece to the insulator using a temperature resistant adhesive is a labor intensive step that increases the complexity and expense of manufacturing the electrosurgical instrument.

Therefore, what is needed is an electrosurgical device that prevents the insulating piece from failing and simplifies the manufacturing process.

BRIEF SUMMARY OF THE INVENTION

The present invention overcomes the disadvantages of the electrosurgical devices in the prior art by providing an electrode with an adhesive-free ceramic piece. In an exemplary embodiment, the electrosurgical instrument includes a probe that can be inserted into a portal during an arthroscopic procedure for ablating tissue.

The distal end of the probe includes an electrode that has one or more active surfaces for ablating or coagulating tissue. The electrode is connected to an electrode seat. In one embodiment, the electrode is connected to the electrode seat using a projection weld. The electrode and the electrode seat can also be made from electrically conductive materials such that they are electrically connected.

An insulating piece is disposed about a portion of the electrode to provide an electrical and/or heat barrier for the non-active portion of the electrode. The insulating piece is configured to leave the active surface of the electrode exposed to the exterior of the electrosurgical device for performing ablation.

The insulating piece is secured to the probe without the use of an adhesive. The electrode has a retaining ledge that is configured to engage a lip on the insulating piece. The electrode engages the insulating piece and is then connected to the electrode seat thereby capturing the insulating piece in between the electrode and the electrode seat. The electrode secures the insulating piece sufficiently that no adhesive is required to secure the insulating piece to the probe.

Securing the insulating piece to the electrosurgical device according to the present invention is beneficial because it does not require the use of an adhesives, which can fail due to the heat created by the active surface. The present invention reduces the failure rate of the insulating piece by capturing the insulating piece between the electrode and the electrode seat. Because the insulating piece relies on the connection (i.e. weld) between the electrode and the electrode seat, rather than an adhesive connection, the insulating piece is less likely to fall off the probe.

Preventing the insulating piece from failing is very desirable because of the potential interruption that can occur during a procedure if the insulating piece fails. As discussed above, when the insulating piece fails, a surgeon ussually attempts to retrieve the piece and has to use a new electrosurgical instrument, thus wasting time and increasing costs. Electrosurgical devices according to the present invention eliminate the risk of an adhesive failing by being mechanically restraining the insulating piece using the electrode.

The electrosurgical device of the present invention is also improved over the prior art because it is easier and cheaper to manufacture. The probe can be assembled in fewer and simpler steps, thus reducing manufacturing costs.

These and other features of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 3, is an exploded view of the probe of the electrosurgical instrument of FIG. 1;

FIG. 4 is a cross-sectional view of the probe of the electrosurgical instrument of FIG. 2;

DETAILED DESCRIPTION OF EXEMPLARY EMBODIMENTS

Figure 1:
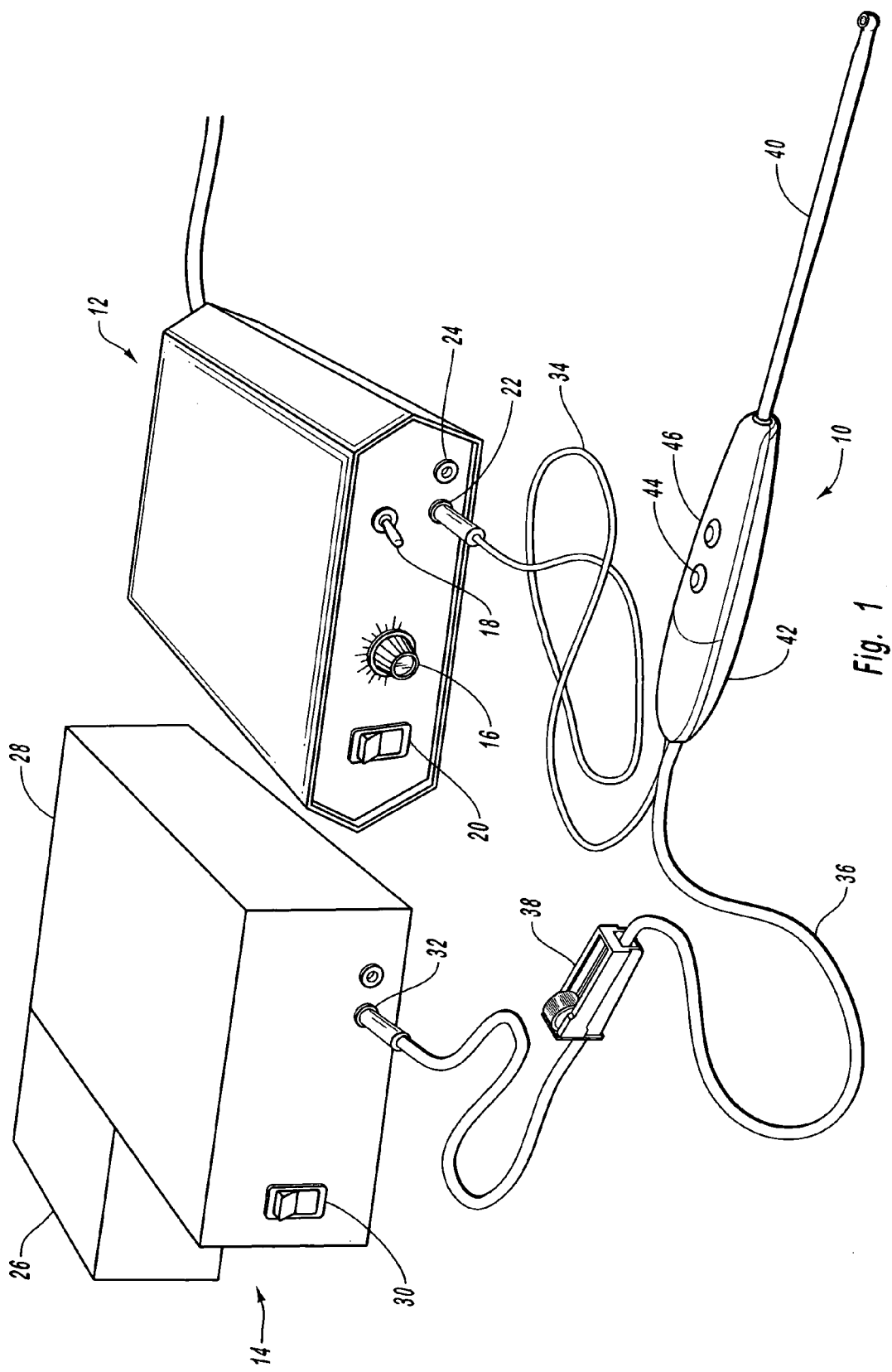
FIG. 1 is a perspective view of an electrosurgical system including a radio frequency generator, an aspirator, and an electrosurgical instrument according to an exemplary embodiment of the present invention.

Embodiments of the present invention relate to electrosurgical systems for ablating tissue in an electrosurgical procedure. FIG. 1 shows an exemplary electrosurgical system which includes an electrosurgical instrument 10 connected to an electrosurgical generator 12 and an aspirator 14.

In an exemplary embodiment, electrosurgical generator 12 is configured to generate radio frequency ("RF") wave forms for a monopolar instrument such as electrosurgical instrument 10. Generator 12 can generate energy useful for ablating tissue and/or coagulating tissue. In one embodiment, generator 12 includes standard components, such as dial 16 for controlling the frequency and/or amplitude of the RF energy, a switch 18 for changing the type of waveform generated, a switch 20 for turning the generator on and off, and an electrical port 22 for connecting the electrosurgical instrument 10. Generator 12 also includes port 24 for connecting an electrical ground. It will be appreciated that generator 12 can be designed for use with bipolar electrosurgical instruments instead of, or in addition to, monopolar devices.

Aspirator pump 14 includes a pump 26, a reservoir 28, an on/off switch 30, and an aspirator port 32. Pump 26 provides negative pressure for aspirating fluids, gasses, and debris through electrosurgical device 10. Aspirated fluids and debris can be temporarily stored in reservoir 28. Those skilled in the art will recognize that many different configurations of generator 12 and aspirator 14 can be used in the present invention.

Electrosurgical instrument 10 includes power cord 34 for electrically connecting instrument 10 to generator 12 through electrical port 22. Extension tubing 36 provides a fluid connection between instrument 10 and aspirator 14. A flow control device 38 allows a practitioner to vary the rate of aspiration through instrument 10.

A probe 40 is connected to a handle 42. Probe 40 can be used for ablating tissue in a patient. Push buttons 44 and 46 on handle 42 can be used to switch the mode of operation of probe 40 between an ablation mode and a coagulation mode.

Figure 2:
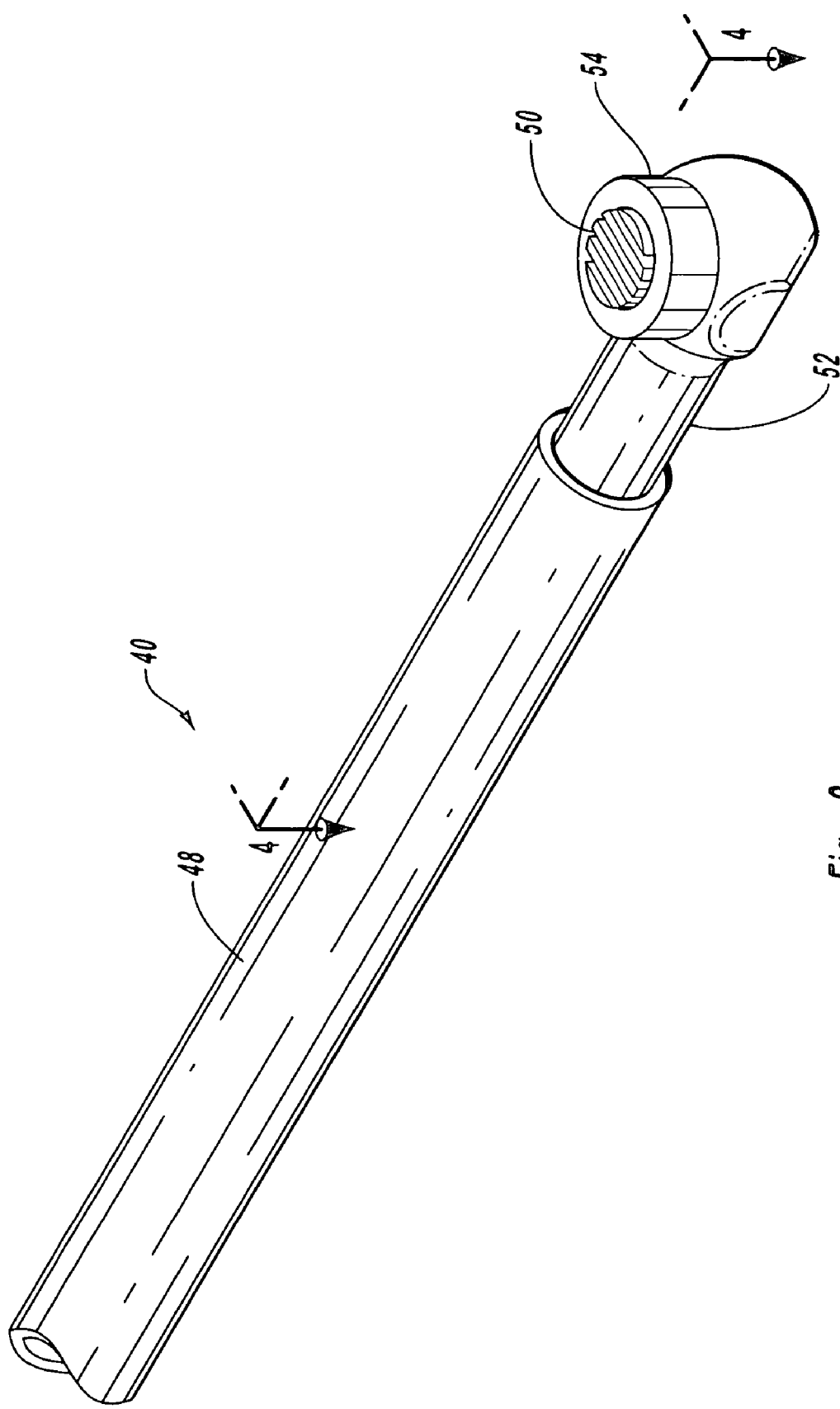
FIG. 2 is a perspective view of the probe of the electrosurgical instrument of FIG. 1.

FIGS. 2 and 3 illustrates probe 40 of the present invention with the insulating layer 56 removed (see FIG. 4) to show various underlying aspects of the invention. As shown in FIG. 2, in an exemplary embodiment, probe 40 includes tubing 48, an electrode 50, an electrode seat 52, and an insulating piece 54.

Electrode 50, shown in FIG. 3, has a proximal end 60 and a distal end 62. Active surface 64 is formed on distal end 62 and is configured to provide arcing for ablating tissue. The edges of active surface 64 create small surface areas where current discharge. The discharge of current from active surface 64 creates a plasma layer that can ablate tissue.

In an alternative embodiment of the present invention, active surface 64 includes a different configuration of electrodes. For example, in one embodiment, the active surface can include wire loops or protruding wires, or any other shape with a surface area small enough to provide sufficient current density for creating an arc or high voltage discharge.

Electrode 50 can also be configured to coagulate tissue. To coagulate tissue the power applied to active surface 64 is reduced such that active surface 64 does not arc. The power applied to active surface 64 creates heat that simply dissipates into surrounding tissue. This heat transfer causes coagulate rather than ablation.

In an exemplary embodiment, insulating piece 54 comprises an annular ring configured to encircle at least a portion of electrode 50. Insulating piece 54 is typically a heat resistant and electrically nonconductive material such as a ceramic. Insulating piece 54 is configured to seat against electrode 50 to prevent undesired discharge of current near active surface 64. Because the temperatures near active surface 64 can reach thousands of degrees Celsius, insulating piece 54 is made of a material that can withstand these temperatures.

While insulating piece 54 has been illustrated as a circular piece with an aperture for placing the electrode 50, insulating piece 54 can be made to have any desired shape. Typically the shape of insulating piece 54 is advantageously designed so as to correspond to the shape of the electrode 50. Insulating piece 54 is usually configured to provide spacing between the active surface 64 and other parts of probe 40.

As shown in FIG. 4, electrode 50, seat 52 and tubing 48 define a lumen 58 through the center of probe 40. Lumen 58 opens near the distal end of electrode 50 for aspirating fluids, gasses, and debris from the exterior of probe 40. On the proximal end of probe 40, lumen 58 is connected to aspirator 14 (See FIG. 1), which creates negative pressure in lumen 58. The negative pressure draws gasses, fluids, and debris from the exterior of instrument 10 into lumen 58. An optional liner 49 within tubing 48 is shown, which can be made of any desired material, including insulating and non-insulating materials.

Probe 40 also includes an insulating coating 56. Insulating coating 56 is typically formed as one or more electrically insulating sheaths. Insulating coating 56 prevents direct electrical contact between the metal components of probe 40 and any exterior materials. Any contact between the conductive components of probe 40 and exterior materials can result in unwanted discharge.

Because of the high temperatures involved in electrosurgery, insulating coating 56 is typically made from a heat resistant material. Suitable materials for making insulating coating 56 include polytetraflouroethylene, polyimides, and the like. In one embodiment, insulating coating 56 includes nylon.

Figure 5:
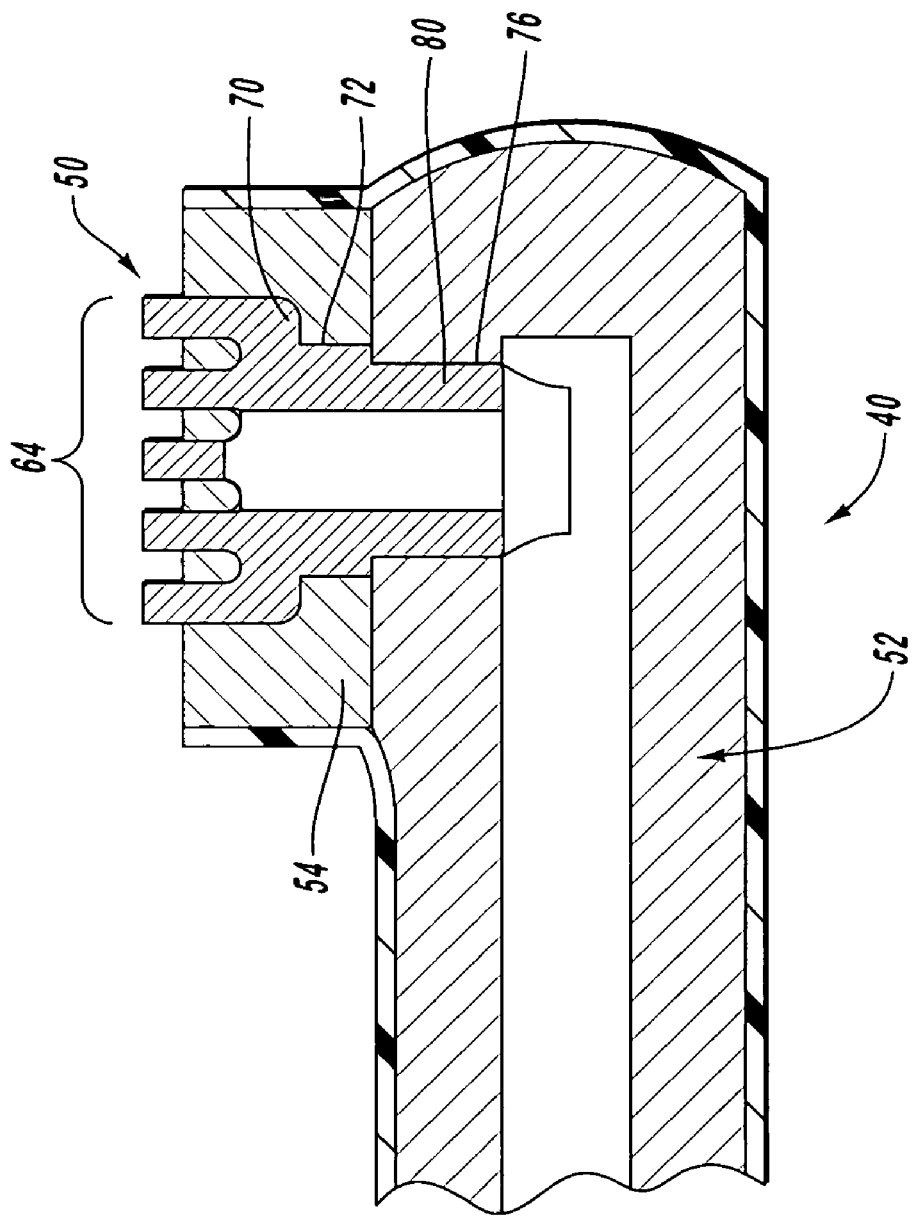
FIG. 5 is a cross-sectional view of the distal end portion of the probe of FIG. 1.

As further shown in FIGS. 3 and 5, electrode 50 is configured to engage insulating piece 54 to secure insulating piece 54 to electrosurgical device 10. Electrode 50 includes a retaining ledge that is configured to engage lip 72 of insulating piece 54. Retaining ledge 70 and lip 72 are configured to seat tightly to minimize the gap between electrode 50 and insulating piece 54. Insulating piece 54 is also seated on surface 76 of electrode seat 52.

In an exemplary embodiment, electrode 50 includes abutment ledge 78. Abutment ledge 78 is configured to engage surface 76 and set electrode 50 at the correct height with respect to electrode seat 52 and insulating piece 54. Typically, abutment ledge 78 is configured to set active surface 64 slightly above insulating piece 54.

Abutment ledge 78 also protects insulating piece 54 from pressure applied to electrode 50 during the manufacturing process, which is discussed more fully below. Insulating piece 52, which is typically made from a ceramic material, can be damaged from excess amounts of pressure. Abutment ledge 78 transfers pressure to electrode seat 52, which is typically made from a metal such as stainless steel or titanium.

In an exemplary embodiment, electrode 50 also includes an insert portion 80. Insert portion 80 is configured to be press fitted into bore 82 of electrode seat 52. Bore 82 can be slightly tapered to create a bore that becomes increasingly tighter for press fitting electrode 50. Alternatively, insert portion 80 can be tapered for press fitting electrode 50 into electrode seat 52.

Connecting electrode 50 to electrode seat 52 secures insulating piece 54 to seat 52. As electrode 50 is placed through insulating piece 54 and into bore 82, retaining ledge 70 engages lip 72. Once electrode 50 is connected to seat 52, the mechanical engagement of insulating piece 54 by electrode 50 secures insulating piece 54 to probe 40.

Retaining ledge 70, which is configured to engage lip 72, is an example of means for retaining insulating piece 54. Other structures can provide suitable means for retaining insulating piece 54. For instance, slots, grooves, pins, and the like that are configured to engage insulating piece 54 are examples of retaining mechanisms suitable for use in the present invention.

Figure 6:
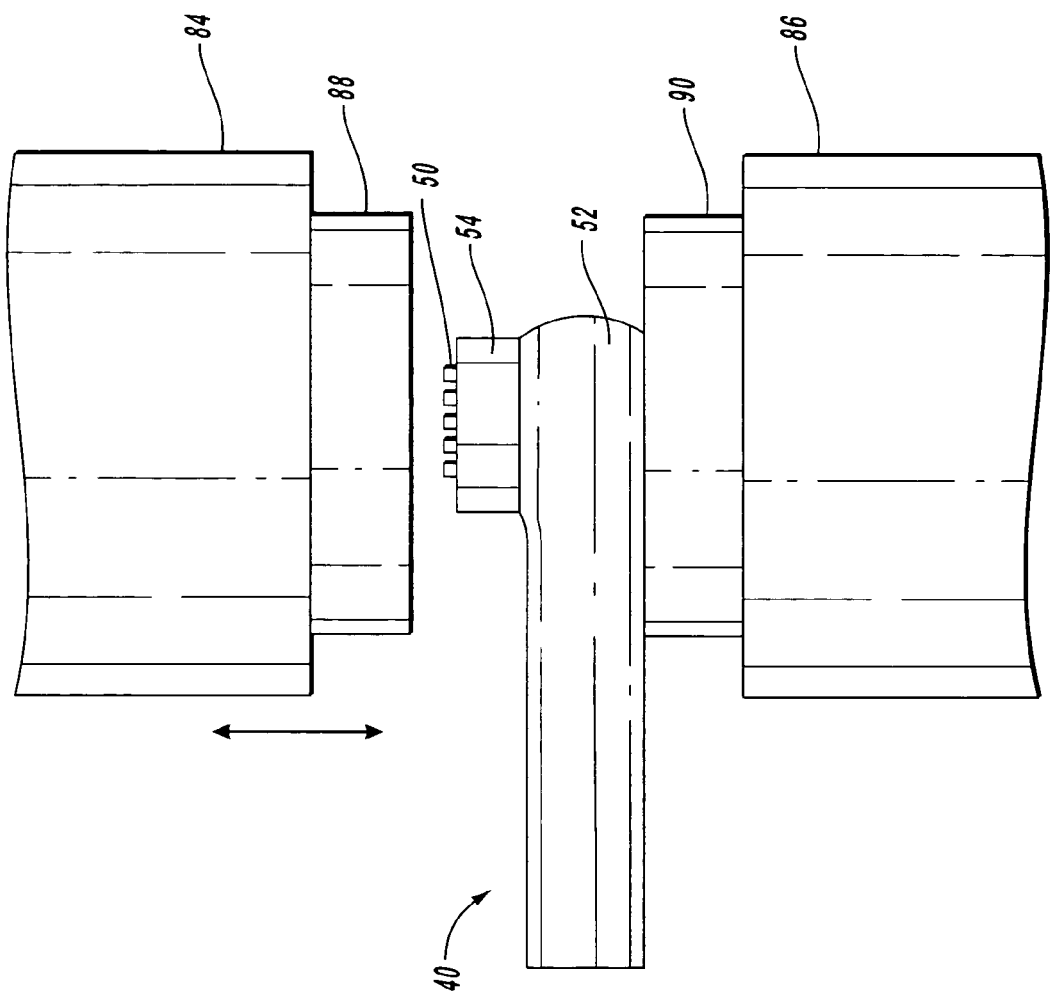
FIG. 6 shows a partial view of a projection welder as it welds the electrode to the electrode seat.

Turning now to FIG. 6, in an exemplary embodiment, electrode 50 is welded to electrode seat 52 using a resistance weld such as a projection weld. FIG. 6 shows a partial view of a typical projection welder, which includes a hydraulic arm 84 and a fixed arm 86. Hydraulic arm 84 and fixed arm 86 include copper heads 88 and 90, respectively. Copper heads 88 and 90 are electrodes connected to a generator that generates a high current. A high current is obtained by using a low voltage such as 1-1.5 Volts. A high current can melt a metal because of the heat created by resistance in the metal.

Electrode 50 and electrode seat 52 are positioned between copper heads 88 and 90 with insulating ring in between. Hydraulic arm 84 is advanced toward electrode 50 until it engages electrode 50 and presses insert portion 80 into bore 82 (See FIG. 3). Current passing through electrode 50 and electrode seat 52 causes a portion of material at the interface to melt and form a weld.

Projection welding takes advantage of the melting point and electrical resistivity of different metals. The greater the resistance of the metal the more heat the metal produces and thus the sooner the metal melts. Of course, the lower the melting point the sooner the metal will melt. Copper is typically used as an electrode for projection welding since copper has low resistance (10.4 ohms (Ohms/CMF)(20° C.)) and a relatively high melting point of 1115° C. Because copper has low resistance and high melting point, it is unlikely to melt and form a weld with the target material.

Pressure between two objects can create additional heat at the point where the pressure is applied. When projection welding electrode 50 to electrode seat 52, the connection can be designed to create pressure in a location where a weld is desired. For example, abutment ledge 78 is configured to be pressed against surface 76 of electrode seat 52. As a high current passes through electrode 50 and electrode seat 52, the pressure between abutment ledge 78 and surface 76 can cause the weld to occur at this seam even though the welder has no direct contact with the seam.

In an alternative embodiment, tapering bore 82 can direct a weld to distal end 60 of electrode 50. Greater pressure is placed on proximal end 60 as insert portion 80 is pressed into bore 82. The pressure causes increased heat and resistance, thereby causing the material to melt and form a weld. Thus, the electrode 50 and electrode seat 52 can be designed to produce a strong weld in a desired location without having direct access to the welding site.

Projection welding is beneficial for connecting electrode 50 to electrode seat 52 since placing insulating piece 54 on electrode 50 blocks access the seam between insulating piece 54 and electrode 50. By using a projection weld, the insulating piece can be mounted on the electrode before the weld between the electrode 50 and seat 52 is made. Because the weld can be made after positioning the insulating piece, the electrode can be designed to capture the insulating piece.

Embodiments of the present invention also include methods for manufacturing electrode 50. Electrode 50 is manufacture by first shaping or forming a piece of electrically conducting material. In an exemplary embodiment, a metal is cut into a cylinder is drilled to form a lumen. An active surface 64 is formed on the distal end for ablating and coagulating tissue. The electrically conducting material can include tungsten, stainless steel or its alloys, platinum or its alloys, titanium or its alloys, molybdenum or its alloys, nickel or its alloys, and the like.

A retainer ledge 70 is formed in electrode 50 by circumferentially grinding the cylinder. Retainer ledge 70 is configured to engage a lip 72 of insulating piece 54. An abutment ledge is formed by further circumferentially grinding electrode 50 distal to retainer ledge 70. Grinding electrode 50 to form retainer ledge 70 also forms insert piece 80. Insert piece 80 is configured to be placed in bore 82 of electrode seat 52.

Insulating piece 54 is placed on electrode 50, which is then connected to electrode seat 52, thereby capturing insulating piece 54 and securing it to probe 40. In one embodiment, the electrode 50 is connected using a projection weld.

Securing insulator piece 54 to the electrosurgical device according embodiments of the present invention is beneficial because it does not require the use of an adhesive. Temperature resistant adhesives are known to fail in a small percentage of cases. While the failure rates of temperature resistant adhesives is somewhat small, even infrequent failures are undesirable. The present invention reduces the failure rate of the insulating piece by capturing the insulating piece between the electrode and the electrode seat. The insulating piece is secured substantially without the use of an adhesive if the mechanical securing mechanism is sufficient to secure the insulating piece without the use of an adhesive.

The electrosurgical device of the present invention is also improved over the prior art because it is easier and cheaper to manufacture. The probe can be assembled in fewer and simpler steps, thus reducing manufacturing costs.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrosurgical instrument comprising:
   an electrode having at least one active surface for ablating or coagulating tissue in an electrosurgical procedure;
   an insulating piece disposed around an outer surface of said electrode to insulate a portion thereof, the insulating piece configured to leave the active surface exposed; and
   an electrode seat to which the electrode is connected;
   a portion of the electrode overhanging a portion of the insulating piece between the electrode and electrode seat so as to mechanically engage the insulating piece to secure the insulating piece to the electrosurgical instrument and prevent detachment of the insulating piece from the electrosurgical instrument.

2. An electrosurgical instrument according to claim 1, wherein the electrode is integrally connected to the electrode seat by a weld.

3. An electrosurgical instrument according to claim 1, wherein the electrode is projection welded to the electrode seat.

4. An electrosurgical instrument according to claim 1, wherein the electrode has a retaining ledge that overhangs and engages a lip on said insulating piece to secure the insulating piece to the electrosurgical instrument and thereby prevent detachment of the insulating piece from the electrosurgical instrument.

5. An electrosurgical instrument according to claim 1, wherein the electrode has an abutment ledge that engages the electrode seat and sets the height of the electrode with respect to the electrode seat.

6. An electrosurgical instrument according to claim 1, wherein the insulating piece comprises a ceramic material.

7. An electrosurgical instrument according to claim 1, wherein the electrode comprises a material selected from the group consisting of tungsten, stainless steel, platinum, titanium, molybdenum, nickel, alloys thereof and combinations thereof.

8. An electrosurgical instrument according to claim 1, wherein the electrode and electrode seat define a lumen therethrough for aspirating gasses and debris generated in an electrosurgical procedure.

9. An electrosurgical instrument comprising:
   an electrode having at least one active surface for cutting or ablating tissue in an electrosurgical procedure;
   an insulating piece disposed around an outer surface of said electrode to insulate a portion thereof, the insulating piece configured to leave the active surface exposed; and
   an electrode seat comprising an electrically conductive material;
   wherein the electrode is integrally connected to the electrode seat by a weld,
   the electrode mechanically securing the insulating piece to the electrosurgical instrument substantially without the use of an adhesive,
   wherein the electrode and electrode seat define a lumen therethrough for aspirating gasses and debris generated in an electrosurgical procedure.

10. An electrosurgical instrument according to claim 9, wherein the electrode is projection welded to the electrode seat.

11. An electrosurgical instrument according to claim 9, wherein the electrode has a retaining ledge that engages a lip on said insulating piece to secure the insulating piece to the electrosurgical instrument.

12. An electrosurgical instrument according to claim 9, wherein the insulating piece comprises a ceramic material.

13. An electrosurgical instrument according to claim 9, wherein the electrode comprises a material selected from the group consisting of tungsten, stainless steel, platinum, titanium, molybdenum, nickel, alloys thereof, and combinations thereof.

14. An electrosurgical instrument comprising:
an electrode seat;
an electrode having at least one active surface for ablating or coagulating tissue in an electrosurgical procedure, the electrode being connected to the electrode seat;
an insulating piece disposed around an outer surface of said electrode to insulate a portion thereof, the insulating piece configured to leave exposed said active surface, the insulating piece being comprised of a heat resistant and electrically non-conductive material so as to provide a heat and electrical barrier; and
means for mechanically securing the insulating piece to the electrosurgical instrument wherein the insulating piece is secured substantially free of an adhesive,
wherein the electrode and electrode seat define a lumen therethrough for aspirating gasses and debris generated in an electrosurgical procedure.

15. An electrosurgical instrument according to claim 14, wherein said means for mechanically securing the insulating piece comprises a retaining ledge on said electrode that engages a lip on said insulating piece.

16. An electrosurgical instrument according to claim 14, wherein the electrode is projection welded to the electrode seat.

17. An electrosurgical instrument comprising:
an electrode having at least one active surface for ablating or coagulating tissue in an electrosurgical procedure;
an insulating piece disposed about said electrode to insulate a portion thereof, the insulating piece configured to leave the active surface exposed; and
an electrode seat to which the electrode is connected;
the electrode engaging the insulating piece to secure the insulating piece to the electrosurgical instrument,
wherein the electrode and electrode seat define a lumen therethrough for aspirating gasses and debris generated in an electrosurgical procedure.

18. An electrosurgical instrument according to claim 17, wherein the electrode is projection welded to the electrode seat.

19. An electrosurgical instrument according to claim 17, wherein the electrode has a retaining ledge that engages a lip on said insulating piece to secure the insulating piece to the electrosurgical instrument.

20. An electrosurgical instrument according to claim 17, wherein the electrode has an abutment ledge that engages the electrode seat and sets the height of the electrode with respect to the electrode seat.

21. An electrosurgical instrument according to claim 17, wherein the insulating piece comprises a ceramic material.

22. An electrosurgical instrument according to claim 17, wherein the electrode comprises a material selected from the group consisting of tungsten, stainless steel, platinum, titanium, molybdenum, nickel, alloys thereof, and combinations thereof.

* * * * *

UNITED STATES PATENT AND TRADEMARK OFFICE
CERTIFICATE OF CORRECTION

PATENT NO. : 7,244,256 B2  Page 1 of 1
APPLICATION NO. : 10/866371
DATED : July 17, 2007
INVENTOR(S) : DeCesare et al.

It is certified that error appears in the above-identified patent and that said Letters Patent is hereby corrected as shown below:

Column 2
Line 64, change "asseyymbled" to --assembled--

Column 3
Line 36, change "adhesives" to --adhesive--
Line 47, change "ussually" to --usually--
Line 51, remove [being]

Column 6
Line 10, change "52" to --54--

Column 7
Line 6, change "60" to --62--
Line 15, after "access" insert --to--
Line 22, change "manufacture" to --manufactured--
Line 25, after "cylinder" insert --and--
Line 44, after "according" insert --to--

Signed and Sealed this

Twenty-fifth Day of December, 2007

JON W. DUDAS
*Director of the United States Patent and Trademark Office*